United States Patent
Greaves

(10) Patent No.: US 12,409,122 B2
(45) Date of Patent: Sep. 9, 2025

(54) PROCESS FOR TREATING KERATIN FIBERS USING A COMPOSITION COMPRISING A CARNITINE SALT OR CARNITINE DERIVATIVE SALT COMPRISING AN AROMATIC ORGANIC ANION

(71) Applicant: L'OREAL, Paris (FR)

(72) Inventor: Andrew Greaves, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 1019 days.

(21) Appl. No.: 17/415,206

(22) PCT Filed: Dec. 19, 2019

(86) PCT No.: PCT/EP2019/086353
§ 371 (c)(1),
(2) Date: Jun. 17, 2021

(87) PCT Pub. No.: WO2020/127767
PCT Pub. Date: Jun. 25, 2020

(65) Prior Publication Data
US 2022/0079860 A1  Mar. 17, 2022

(30) Foreign Application Priority Data

Dec. 20, 2018 (FR) .................................. 1873579

(51) Int. Cl.
*A61K 8/44* (2006.01)
*A61K 8/365* (2006.01)
*A61K 8/368* (2006.01)
*A61K 8/46* (2006.01)
*A61K 8/55* (2006.01)
*A61Q 5/00* (2006.01)
*A61Q 5/02* (2006.01)
*A61Q 5/12* (2006.01)

(52) U.S. Cl.
CPC ................ *A61K 8/44* (2013.01); *A61K 8/368* (2013.01); *A61Q 5/002* (2013.01)

(58) Field of Classification Search
CPC ......... A61K 8/44; A61K 8/368; A61K 8/466; A61K 8/55; A61K 8/365; A61Q 5/002; A61Q 5/02; A61Q 5/12
See application file for complete search history.

(56) References Cited

U.S. PATENT DOCUMENTS

| | | | | |
|---|---|---|---|---|
| 5,741,816 A | * | 4/1998 | Tsujihara | C07C 229/22 514/552 |
| 2008/0118458 A1 | | 5/2008 | Giesen et al. | |
| 2013/0172414 A1 | * | 7/2013 | Wang | A61K 31/095 514/556 |
| 2018/0064619 A1 | | 3/2018 | Brun et al. | |

FOREIGN PATENT DOCUMENTS

| | | |
|---|---|---|
| CN | 102512409 A | 6/2012 |
| DE | 19539859 A1 | 4/1997 |
| EP | 0978272 A1 | 2/2000 |
| EP | 1175898 A2 | 1/2002 |
| EP | 1800654 A2 | 6/2007 |
| EP | 2111852 A2 | 10/2009 |
| EP | 2165697 A1 | 3/2010 |
| FR | 2619007 A1 | 2/1989 |
| JP | H08-092180 A | 4/1996 |
| JP | 2003-526661 A | 9/2003 |
| JP | 2011-132191 A | 7/2011 |
| JP | 2011-132192 A | 7/2011 |
| KR | 10-2017-0014179 A | 2/2017 |
| WO | 98/30196 A1 | 7/1998 |
| WO | 02/074265 A1 | 9/2002 |
| WO | 2006/097205 A2 | 9/2006 |
| WO | 2007/003307 A1 | 1/2007 |
| WO | 2016/151139 A1 | 9/2016 |
| WO | 2018/218009 A2 | 11/2018 |
| WO | 2020/127764 A1 | 6/2020 |

OTHER PUBLICATIONS

JP2011132192A—Google English Translation (Year: 2011).*
Translation of Japanese Office Action for counterpart Application No. 2021-530964, dated Jun. 6, 2022.
Translation of Japanese Office Action for counterpart Application No. 2021-531402, dated Jul. 4, 2022.
International Search Report and Written Opinion for counterpart Application No. PCT/EP2019/086348, dated Apr. 6, 2020.
International Search Report and Written Opinion for counterpart Application No. PCT/EP2019/086353, dated Apr. 9, 2020.
McMichael, Amy J., "Hair Breakage in Normal and Weathered Hair: Focus on the Black Patient," Journal of Investigative Dermatology Symposium Proceedings, vol. 12, Issue 2, Dec. 2007, pp. 6-9.
Swift, J. Alan, et al., "Flexabrasion: A Method for Evaluating Hair Strength," Cosmetics and Toiletries Journal, vol. 116, Dec. 12, 2001, pp. 53-60.
Translation of Chinese Office Action for counterpart Application No. 201980082950.4, dated Nov. 2, 2022.
Translation of Chinese Office Action for counterpart Application No. 201980083854.1, dated Nov. 2, 2022.
Non-Final Office Action in U.S. Appl. No. 17/415,602, mailed Jul. 17, 2024, 11 pages.
Restriction Requirement for copending U.S. Appl. No. 17/415,602, dated Apr. 12, 2024.
Final Office Action in U.S. Appl. No. 17/415,602, mailed Dec. 12, 2024, 10 pages.

* cited by examiner

*Primary Examiner* — Kyung S Chang
(74) *Attorney, Agent, or Firm* — THE MARBURY LAW GROUP, PLLC

(57) ABSTRACT

The present invention relates to a process for treating keratin fibers, comprising the application of a composition comprising at least one carnitine salt or carnitine derivative salt comprising an aromatic organic anion, for caring for and/or repairing keratin fibers.

7 Claims, No Drawings

PROCESS FOR TREATING KERATIN FIBERS USING A COMPOSITION COMPRISING A CARNITINE SALT OR CARNITINE DERIVATIVE SALT COMPRISING AN AROMATIC ORGANIC ANION

CROSS REFERENCE TO RELATED APPLICATION

This is a national stage application of PCT/EP2019/086353, filed internationally on Dec. 19, 2019, which claims priority to French Application No. 1873579, filed on Dec. 20, 2018, both of which are incorporated by reference herein in their entireties.

TECHNICAL FIELD

The present invention relates to a process for treating keratin fibers, comprising the application of a composition comprising at least one carnitine salt or carnitine derivative salt comprising an aromatic organic anion, for caring for and/or repairing keratin fibers.

CONTEXT

The hair can be damaged and weakened by external atmospheric agents such as pollution and bad weather, and also by mechanical or chemical treatments, such as brushing, combing, dyeing, bleaching, permanent-waving, relaxing and repeated washing. The hair can be damaged and in the long term can become brittle.

Thus, in order to remedy this, it is usual to have recourse to hair compositions intended for conditioning the hair. However, the conditioning effect obtained via these hair treatments fades out rapidly over time, and does not have satisfactory persistence with respect to shampoo washes.

It is known that carnitine or a salt thereof, such as carnitine tartrate or carnitine lactate, can be used in hair compositions (see in particular DE 195 39 859, EP 1 800 654 and EP 2 111 852. Likewise, it is known that certain organic acids can be used in hair compositions (see in particular EP 0 978 272). However, these compounds are not always entirely satisfactory with regard to preventing the breakage of the hair, in particular during combing.

There is therefore a still a real need to develop a process for treating the hair which makes it possible to preserve or even improve the quality of the fiber in order to reduce the breakage thereof, in particular during combing and in a long-lasting manner, that is to say which exhibits satisfactory persistence with respect to shampoo washes.

The applicant has discovered, surprisingly, that all of these problems can be solved by the process according to the present invention involving the application to the hair of a composition comprising carnitine salts or carnitine derivative salts having one or more aromatic organic anions.

SUMMARY

According to a first aspect, a subject of the present invention is a process for treating keratin fibers, comprising:
(i) a step of applying to the keratin fibers a composition (A) comprising at least one compound of formula (I):

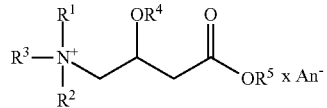

and the solvates thereof such as hydrates;
formula (I) wherein
$R^1$, $R^2$ and $R^3$, which may be identical or different, represent a $(C_1-C_4)$alkyl group or $(C_1-C_4)$hydroxyalkyl group;
$R^4$ represents a hydrogen atom, a $(C_1-C_4)$alkyl group or a —C(O)R group, wherein R is a $(C_1-C_3)$alkyl group;
$R^5$ represents a hydrogen atom, a $(C_1-C_4)$alkyl group, an alkali metal or an alkaline-earth metal;
$An^-$ represents an aromatic organic anion selected from the compounds of formula (II), (III) or (IV) below:

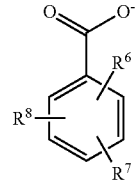

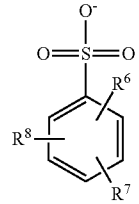

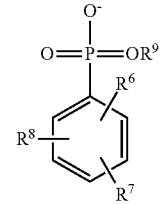

wherein:
$R^6$, $R^7$ and $R^8$, which may be identical or different, represent a hydrogen atom or a group chosen from hydroxyl, $(C_1-C_4)$alkyl or $(C_1-C_4)$alkoxyl;
$R^9$ represents a hydrogen atom, a negative charge, an alkali metal or an alkaline-earth metal;
x is a stoichiometric coefficient chosen so as to guarantee the electrical neutrality of the compound of formula (I).

According to a second aspect, a subject of the present invention is a composition (A) as defined above.

According to a third aspect, a subject of the present invention is the compounds of formula (Ib), (Ic), (Id) or (Ie) below:

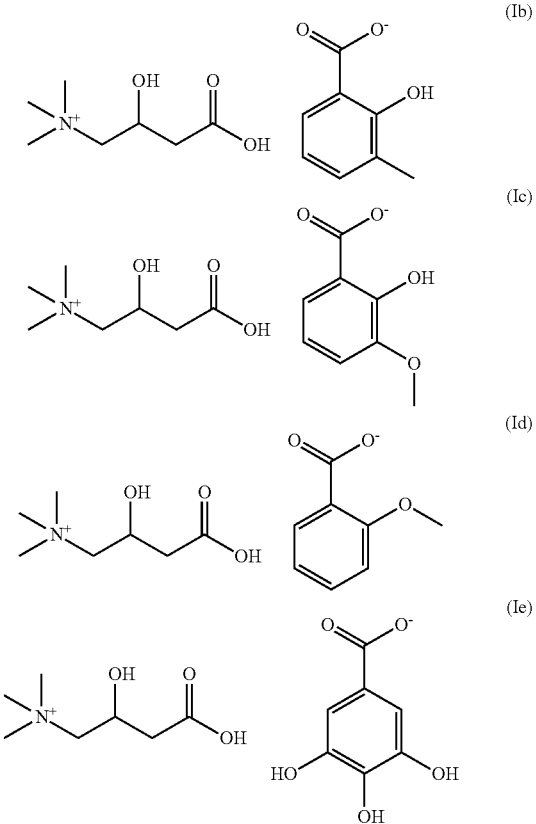

According to a fourth aspect, a subject of the present invention is the cosmetic use of at least one compound of formula (I), as defined above, for caring for and/or repairing keratin fibers.

According to a final aspect, a subject of the present invention is the cosmetic use of at least one composition (A), as defined above, for caring for and/or repairing keratin fibers.

DETAILED DESCRIPTION

The term "keratin fibers" is intended to mean fibers of human or animal origin, such as the hair, body hair, the eyelashes, the eyebrows, wool, angora, cashmere or fur. According to the present invention, the keratin fibers are preferably human keratin fibers, more preferentially the hair.

The term "alkyl group" is intended to mean a linear or branched radical containing from 1 to 12 carbon atoms.

The term "$(C_1$-$C_4)$alkyl group" is intended to mean an alkyl group comprising from 1 to 4 carbon atoms, preferably methyl, ethyl, n-propyl, isopropyl or butyl, more preferentially methyl or n-propyl, even more preferentially methyl.

The term "$(C_1$-$C_3)$alkyl group" is intended to mean an alkyl group comprising from 1 to 3 carbon atoms, preferably methyl, ethyl, n-propyl or isopropyl, more preferentially methyl or n-propyl, even more preferentially methyl.

The term "$(C_1$-$C_4)$hydroxyalkyl group" is intended to mean a $(C_1$-$C_4)$alkyl group, at least one of the hydrogen atoms of which is replaced with a hydroxyl (—OH) group.

The term "alkoxyl group" is intended to mean an alkyl group bonded to a hydrogen atom.

The term "$(C_1$-$C_4)$alkoxyl group" is intended to mean an alkoxyl group comprising from 1 to 4 carbon atoms.

The expression "at least one" is synonymous with the expression "one or more".

The expression "preventing the breakage of keratin fibers" is synonymous with the expression "increasing the mechanical strength of keratin fibers".

Treatment Process

According to a first aspect, a subject of the present invention is a process for treating keratin fibers as described above. Preferably, the treatment process may be a process for caring for and/or repairing keratin fibers.

The applicant has discovered, surprisingly, that the use of carnitine or of a derivative thereof in combination with certain aromatic organic anions having a carboxylate, sulfonate or phosphonate group, in the process according to the invention, makes it possible to improve the mechanical strength of keratin fibers and thus to reduce the breakage thereof, in particular during combing. Moreover, the applicant has also observed that it is possible to obtain a long-lasting effect over time with in particular a satisfactory persistence with respect to shampoo washes.

Composition (A)

According to a second aspect, a subject of the present invention is also a composition (A) as described above.

The composition (A) comprises at least one compound of formula (I) as defined above. The compound of formula (I) is a carnitine salt or a salt of a derivative thereof. The cationic portion of the compound of formula (I) is carnitine or a derivative thereof and the anionic portion $An^-$ of the compound of formula (I) is an aromatic organic anion.

Anionic Portion $An^-$ represents an aromatic organic anion selected from the compounds of formula (II), (III) or (IV) below:

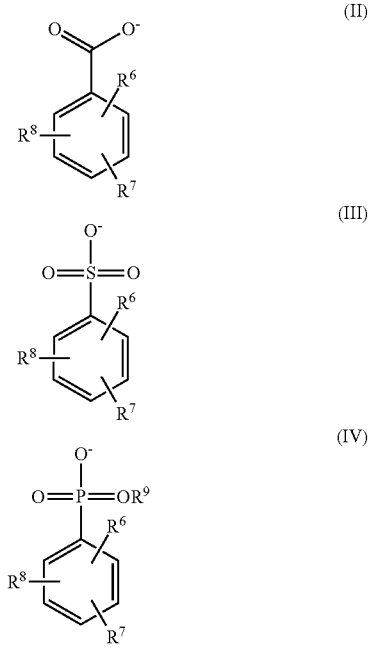

wherein:
  $R^6$, $R^7$ and $R^8$, which may be identical or different, represent a hydrogen atom or a group chosen from hydroxyl, $(C_1$-$C_4)$alkyl or $(C_1$-$C_4)$alkoxyl;
  $R^9$ represents a hydrogen atom, a negative charge, an alkali metal or an alkaline-earth metal.

Preferably, $R^9$ represents a negative charge.

In the case where $An^-$ is selected from the compounds of formula (II) or (III) or of formula (IV) wherein $R^9$ represents a hydrogen atom, the stoichiometric coefficient x is equal to 1, in such a way as to guarantee the electrical neutrality of the compound (I). Alternatively, in the case where An⁻ is selected from the compounds of formula (IV) wherein $R^9$ represents a negative charge, the stoichiometric coefficient x is equal to 0.5, in such a way as to guarantee the electrical neutrality of the compound (I).

The composition (A) may comprise a mixture of compounds of formula (I) comprising different aromatic organic anions An⁻ selected from the compounds of formula (II), (III) or (IV) as defined above.

An⁻ can preferably be selected from the compounds of formula (II'), (III') or (IV') below:

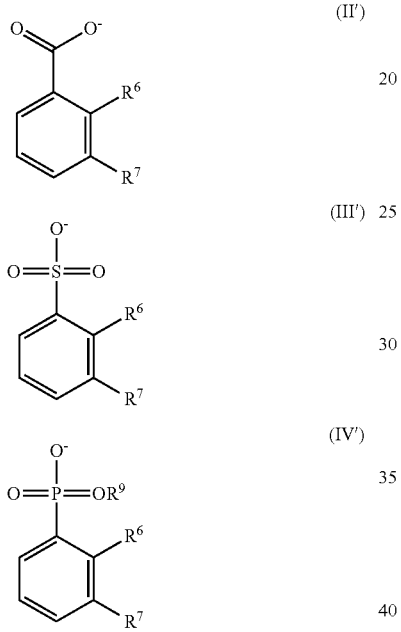

wherein:
- $R^6$ and $R^7$, which may be identical or different, represent a hydrogen atom or a group chosen from hydroxyl, $(C_1-C_4)$alkyl or $(C_1-C_4)$alkoxyl;
- $R^9$ represents a hydrogen atom, a negative charge, an alkali metal or an alkaline-earth metal, preferably a negative charge.

The composition (A) may comprise a mixture of compounds of formula (I) comprising different aromatic organic anions An⁻ selected from the compounds of formula (II'), (III') or (IV') as defined above.

Advantageously, $R^6$ can represent a group chosen from hydroxyl or $(C_1-C_4)$alkoxyl and $R^7$ can represent a hydrogen atom or a group chosen from $(C_1-C_4)$alkyl or $(C_1-C_4)$alkoxyl.

Advantageously, $R^6$ can represent a group chosen from hydroxyl or methoxyl and $R^7$ can represent a hydrogen atom or a group chosen from $(C_1-C_4)$alkyl or $(C_1-C_4)$alkoxyl, preferably a hydrogen atom or a group chosen from methyl or methoxyl.

An⁻ can preferably be selected from the compounds of formula (II"), (III") or (IV") below:

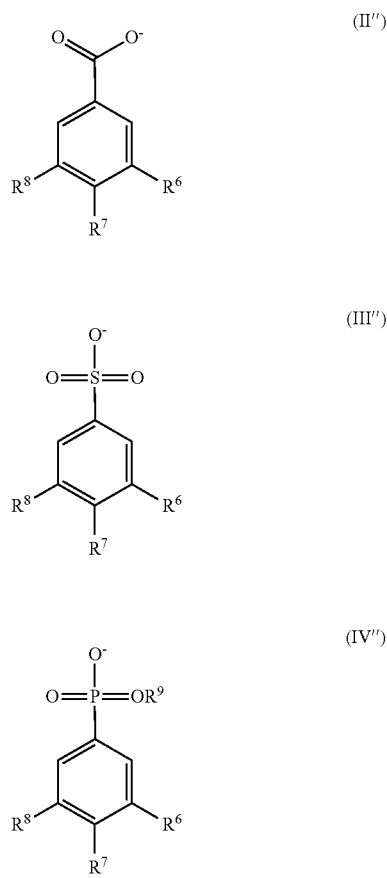

wherein:
- $R^6$, $R^7$ and $R^8$, which may be identical or different, represent a hydrogen atom or a group chosen from hydroxyl, $(C_1-C_4)$alkyl or $(C_1-C_4)$alkoxyl;
- $R^9$ represents a hydrogen atom, a negative charge, an alkali metal or an alkaline-earth metal, preferably a negative charge.

Advantageously, $R^6$, $R^7$ and $R^8$ represent a hydroxyl group.

Preferably, An⁻ can be selected from the compounds of formula, (II') or (II") as defined above. More preferentially, An⁻ can be selected from the compounds of formula (II') or (II") as defined above. Even more preferentially, An⁻ can be selected from the compounds of formula (II').

Cationic Portion

In the case where $R^5$ represents an alkali metal, it may be sodium.

The compound of formula (I) can preferably be a carnitine salt. Thus, $R^1$, $R^2$ and $R^3$ can preferably represent a methyl group and $R^4$ and $R^5$ can preferably represent a hydrogen atom.

The cationic portion of the compound of formula (I) can preferably be in the form of an optical isomer of L (levorotatory) or D (dextrorotatory) configuration, more preferentially of L configuration.

The compound of formula (I) can be selected from the compounds of formula (Ia), (Ib), (Ic), (Id) or (Ie) below and mixtures thereof:

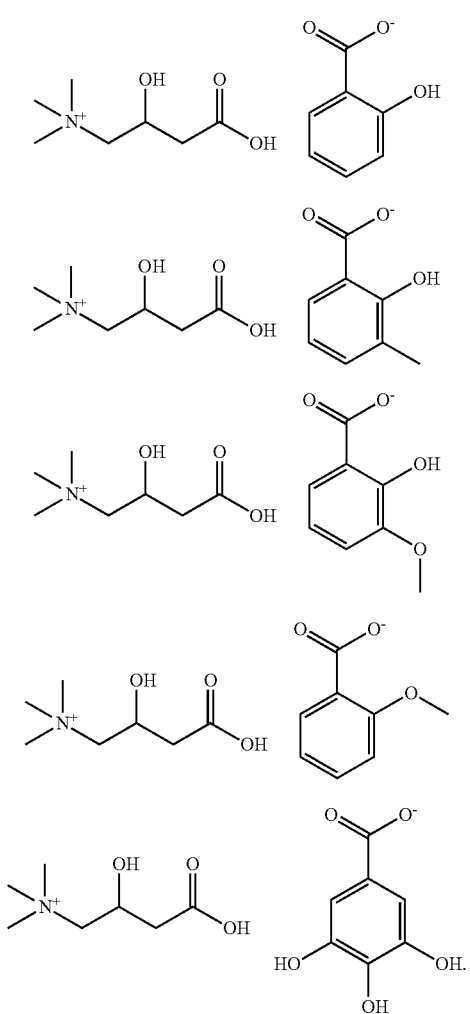

The composition (A) can comprise a total content of compound(s) of formula (I) ranging from 0.1% to 100%, preferably from 0.5% to 50%, more preferentially from 0.5% to 20%, even more preferentially from 1% to 10% by weight relative to the total weight of the composition (A).

Other Elements/Ingredients

The composition (A) used in the process according to the present invention is a cosmetic composition, i.e. a composition which comprises a cosmetically acceptable medium, that is to say a medium compatible with human keratin fibers.

The composition (A) can comprise a solvent selected from the group constituted of water, $C_2$-$C_4$ alcohols, polyols, polyol ethers, and mixtures thereof. In this case, the compound of formula (I) can in particular be in dissociated form in the composition (A).

The composition (A) can comprise a solvent selected from the group constituted of water, ethanol, isopropanol, glycerol, propylene glycol, butylene glycol, pentylene glycol, hexylene glycol, dipropylene glycol, diethylene glycol, 2-butoxyethanol, propylene glycol monomethyl ether, diethylene glycol monoethyl ether, diethylene glycol monomethyl ether, and mixtures thereof.

Preferably, the composition (A) can comprise a solvent selected from the group constituted of water, ethanol, isopropanol, and mixtures thereof.

More preferentially, the composition (A) can comprise a solvent selected from the group constituted of water, ethanol, and mixtures thereof.

The composition (A) can advantageously comprise a water/ethanol mixture comprising at least 10%, from at least 20%, more preferentially at least 30% by weight of ethanol. According to the latter embodiment, the composition (A) can in particular be formulated in the form of a lotion applied to dry keratin fibers, the use of ethanol making it possible to facilitate the wetting of the dry keratin fibers, the drying of the keratin fibers thus treated and also the diffusion of the active agents in the keratin fibers.

The composition (A) can also comprise at least one cosmetic ingredient selected from the group constituted of nonionic, anionic, cationic and amphoteric surfactants, vitamins and provitamins, including panthenol, fillers, colorants, nacreous agents, opacifiers, sequestrants, film-forming polymers, cationic, anionic or neutral polymers, associative polymers, plasticizers, silicones, thickeners, oils, antifoams, moisturizers, emollients, penetrants, fragrances, preserving agents, and mixtures thereof.

These usual cosmetic ingredients can be present in the composition (A) in usual amounts, which can be easily determined by those skilled in the art, and which can range, each ingredient, from 0.01% to 20% by weight relative to the total weight of the composition (A). Those skilled in the art will take care to select the ingredients included in the composition (A), and also the amounts thereof, so that they do not harm the properties of the composition.

The composition (A) can be in any galenical form conventionally used for a hair application. In a nonlimiting manner, the composition (A) can be in the form of a lotion, a cream, a foam, a gel, spray or a lacquer.

The composition (A) can be used by rinse-off or leave-on application.

The composition (A) can be in the form of a shampoo, a mask, a conditioning composition or a pre-shampoo. The composition (A) can also be in the form of a composition to be added to or mixed with, before application, a shampoo, a mask or a conditioning composition.

The composition (A) can be packaged in a pump dispenser bottle or in an aerosol container, in order to ensure application of the composition (A) in vaporized form (lacquer) or in foam form. In these cases, the composition (A) preferably comprises at least one propellant.

pH of the Composition (A)

The composition (A) have a pH ranging from 3 to 10, preferably from 4 to 7. The pH can be adjusted using an organic or mineral base or an organic or mineral base normally used in the cosmetics industry.

Additional Characteristics Regarding the Process

The composition (A) may be applied to dry or wet keratin fibers, and preferably to dry keratin fibers.

The bath ratio of the composition (A) applied to the keratin fibers can range from 0.1 to 10. The term "bath ratio" is intended to mean the ratio between the total weight of the applied composition (A) and the total weight of keratin fibers to be treated.

The process according to the present invention may comprise at least one additional step following on from step i) selected from the following steps ii) to iv):

ii) a step of leaving the composition (A) on the keratin fibers, preferably for a period of at least 10 seconds;

iii) a step of rinsing and/or washing the keratin fibers;

iv) a step of drying the keratin fibers in ambient air or by means of a heating device.

Preferably, the process may comprise the additional steps i) and iv) as described above and carried out in that order. More preferentially, the process may comprise all of the additional steps ii), iii) and iv) as described above and carried out in that order.

The leaving on step can have a duration ranging from 10 seconds to 60 minutes, preferably from 30 seconds to 30 minutes.

The washing step may for example be carried out using a shampoo.

The temperature of the heating means may range from 45° C. to 230° C., preferably from 45° C. to 100° C., more preferentially from 50° C. to 80° C. A hairdryer, a heating hood, an iron or a heating brush may for example be used as heating means.

In the case where the process does not comprise step iii) of rinsing and/or washing the keratin fibers, the composition (A) may for example comprise a water/ethanol mixture which comprises at least 10%, preferably at least 20%, more preferentially at least 30% by weight of ethanol. The use of such a mixture makes it possible in particular to facilitate the evaporation of the composition.

Compounds

According to a third aspect, a subject of the present invention is the compounds of formula (Ib), (Ic), (Id) or (Ie) below and mixtures thereof:

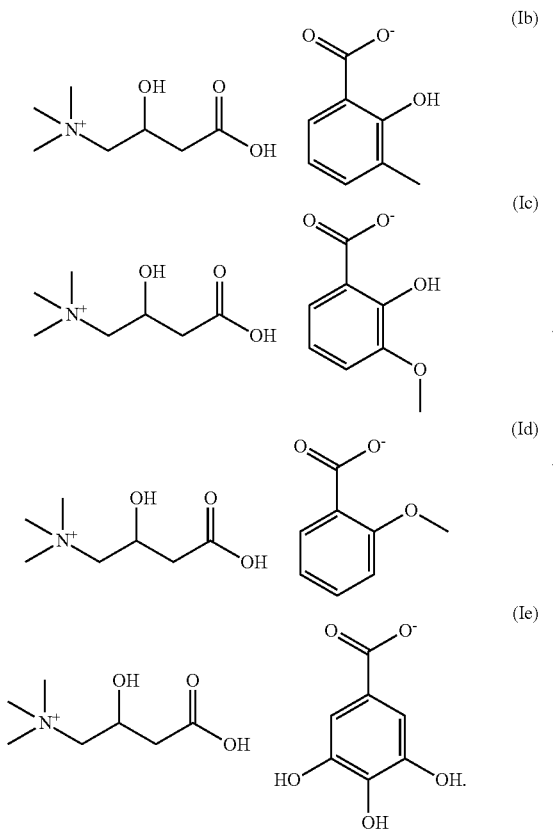

Uses

According to a fourth aspect, a subject of the present invention is the cosmetic use of at least one compound (I), as defined above, for caring for and/or repairing keratin fibers, preferably for preventing the breakage of keratin fibers. Any of the compounds (I) described above can be used for this purpose.

According to a final aspect, a subject of the present invention is the cosmetic use of a composition (A), as defined above, for caring for and/or repairing keratin fibers, preferably for preventing the breakage of keratin fibers.

The examples that follow serve to illustrate the invention without, however, being limiting in nature.

EXAMPLES

In the text which follows, the term "alkaline solubility (AS)" is intended to mean the loss of mass of a sample of 100 mg of keratin fibers under the action of a decinormal sodium hydroxide solution for 30 min at 65° C.

Preparation of the Carnitine Salts Used in the Examples

Carnitine Salicylate

The carnitine salicylate was prepared according to the procedure described below:

Procedure 250 g of L-carnitine (M=161.19 g/mol; CAS: 541-15-1), i.e. 1.55 mol, are weighed out into a flask and then 214.45 g of solid salicylic acid (M=138.27 g/mol; CAS: 69-72-7), i.e. 1.55 mol, are added. 20 ml of water and 60 ml of ethanol are added. The mixture is stirred. The mixture is heated in a water bath (bath temperature of 50° C.) until complete solubilization of the compounds. The resulting solution is stirred at ambient temperature for 30 min. The solvents are evaporated off, then the resulting product is placed in a desiccator (T=40° C.) until the mass is constant.

Result $m_{obtained}$: 422.37 g

Carnitine 3-Methylsalicylate

The carnitine 3-methylsalicylate was prepared according to the procedure described below:

Procedure 50 g of L-carnitine (M=161.19 g/mol; CAS: 541-15-1), i.e. 310 mmol, are weighed out into a single-necked flask and then 47.19 g of 3-methylsalicylic acid (M=152.15 g/mol; CAS: 83-40-9), i.e., 310 mmol, are added. 50 ml of water and 30 ml of ethanol are added. The mixture is stirred for 5 minutes. The resulting mixture is transferred into a pair-shaped flask, the walls are rinsed with ethanol and vacuum evaporation is performed.

Result $m_{obtained}$: 96 g

Carnitine 2-Hydroxy-3-Methoxybenzoate

The carnitine 2-hydroxy-3-methoxybenzoate was prepared according to the procedure described below:

Procedure 50 g of L-carnitine (M=161.19 g/mol; CAS: 541-15-1), i.e., 310 mmol, are weighed out into a single-necked flask.

52.15 g 2-hydroxy-3-methoxybenzoic acid (M=168.15 g/mol; CAS: 877-22-5), i.e., 310 mmol, are added. 30 ml of water and 20 ml of ethanol are added. The resulting solution is stirred at ambient temperature for 30 min. Vacuum evaporation is performed, then the resulting product is placed in a desiccator (T 40° C.) until the mass is constant.

Result $m_{obtained}$: 101.2 g

Carnitine 2-Methoxybenzoate

The carnitine 2-methoxybenzoate was prepared according to the procedure described below:

Procedure 50 g of L-carnitine (M=161.19 g/mol; CAS: 541-15-1), i.e., 310 mmol, are weighed out into a single-necked flask. 47.19 g of 2-methoxybenzoic acid (M=152.15 g/mol; CAS: 579-75-9), i.e., 310 mmol, are added. 40 ml of water and 30 ml of ethanol are added and the resulting mixture is stirred for 30 min, then vacuum evaporation is performed.

Result $m_{obtained}$: 97 g

Carnitine Gallate

The carnitine gallate was prepared according to the procedure described below:

Procedure 20 g of L-carnitine (M=161.19 g/mol; CAS: 541-15-1), i.e. 124 mmol, and 20 ml of water are weighed out into a flask. A solution of 21.1 g of solid gallic acid (M=170.12 g/mol; CAS: 149-91-7), i.e. 124 mmol, in 65 ml of ethanol is then added dropwise. The mixture is stirred. The mixture is heated in a water bath (bath temperature of 50° C.) until complete solubilization of the compounds. The resulting solution is stirred at ambient temperature for 30 min. The solvents are evaporated off, then the resulting product is placed in a desiccator (T=40° C.) until the mass is constant.

Result $m_{obtained}$: 42 g (beige wax)

Comparative Tests No. 1: Comparison of Carnitine Salicylate vs. Carnitine Tartrate—Study of the "Prevention of Breakage Due to Repeated Combing" Effect Formulae Tested:

The following formulae were prepared and then tested according to the procedure described below:

TABLE 1

|  | Formulae | |
| --- | --- | --- |
| Ingredients | 1 (Invention) | 2 (comparative) |
| Carnitine salicylate | 10 g | |
| Carnitine tartrate | | 10 g |
| Water | qs 100 g | qs 100 g |

Procedure

Place three locks of damaged hair (2.7 g/25 cm; alkaline solubility of 60) on a hot plate kept at a temperature of 27° C. and covered with a food film. Apply 0.5 g of formula (formula 1 or 2) to be tested/g of hair to two distinct locks. Spread the formula to be tested over the lock using a small brush. Leave to stand for 5 minutes. Dry under a hood (60° C., 10 min/g hair). Repeat the steps so as to have a total of 5 applications of the formula to be tested. Leave the locks suspended vertically for 24 h. Then comb the locks 30 times with a comb at a rate of 10 cm/s. Weigh the mass of hair lost during the combing.

Results

TABLE 2

| Formulae | Loss (g) |
| --- | --- |
| 1 (Invention) | 0.1647 |
| 2 (Comparative) | 0.3173 |

The results show that there is less hair breakage when the locks are treated by means of a process according to the present invention.

Comparative Tests No. 2: Comparison with Respect to Example 11 of EP0978272 A1—Study of the "Prevention of Breakage Due to Repeated Combing" Effect Formulae Tested:

The following formulae were prepared and then tested according to the procedure described below:

TABLE 3

| | Formulae | | | |
| --- | --- | --- | --- | --- |
| Ingredients | 3 (Comparative) Example 11 of EP0978272 | 4 (Comparative) Example 11 with replacement of malic acid with carnitine at malic acid molar eq. | 5 (Comparative) Example 11 with replacement of malic acid with salicylic acid at malic acid molar eq. | 6 (Invention) Example 11 with replacement of malic acid with carnitine salicylate at malic acid molar eq. |
| Malic acid | 1.28 g (=4 g %, 9.54 mmol) | | | |
| 2-Benzyloxy-ethanol | 3.2 g | 3.2 g | 3.2 g | 3.2 g |
| Ethanol | 4.8 g | 4.8 g | 4.8 g | 4.8 g |
| Mono-ethanolamine | 1.6 g | 1.6 g | 1.6 g | 1.6 g |
| Carnitine | | 1.54 g (9.54 mmol) | | |
| Salicylic acid | | | 1.31 g (9.54 mmol) | |
| Carnitine salicylate | | | | 2.85 g (9.54 mmol) |
| pH modifier (NaOH/HCl) | qs pH 3 | qs pH 3 | qs pH 3 | qs pH 3 |
| Water | qs 32 g | qs 32 g | qs 32 g | qs 32 g |

Procedure

Place four locks of damaged hair (2.7 g/25 cm; alkaline solubility of 60) on a hot plate kept at a temperature of 40°

C. and covered with a food film. Apply 10 g of formula (formula 3 or 4 or 5 or 6) to be tested/g of hair to four distinct locks. Spread the formula to be tested over the lock using a small brush. Leave to stand for 60 minutes. Remove the film. Wash each of the locks with DOP shampoo according to the washing protocol described below. Dry under a hood (60° C., 10 min/g hair). Leave the locks suspended vertically for 24 h. Then comb the locks 30 times with a comb at a rate of 10 cm/s. Weigh the mass of hair lost during the combing.

Washing Protocol:

Wet the locks with tap water at 38° C. for 10 seconds, apply the shampoo (0.4 g/g of hair), massage for 15 seconds and rinse carefully with water for 20 seconds. Wring the locks dry. Comb.

Results

TABLE 4

| Formulae | Loss (g) |
| --- | --- |
| 3 (Comparative) | 0.3842 |
| 4 (Comparative) | 0.3594 |
| 5 (Comparative) | 0.3696 |
| 6 (Invention) | 0.1909 |

There is less hair breakage when the locks are treated by means of a process according to the present invention.

Comparative Tests No. 3: Comparison of Carnitine Salicylate vs. Malic Acid and Lactic Acid—Study of the "Prevention of Breakage Due to Repeated Combing" Effect Formulae Tested:

The following formulae were prepared and then tested according to the procedure described below:

TABLE 5

| Ingredients | Formulae | | | | |
| --- | --- | --- | --- | --- | --- |
| | 7 (Comparative) | 8 (Comparative) | 9 (Comparative) | 10 (Invention) | 11 (Comparative) |
| Malic acid | 4.47 g (33 mmol) | | | | |
| Lactic acid | | | | | 3.01 g (33 mmol) |
| Salicylic acid | | 4.61 g (33 mmol) | | | |
| Carnitine | | | 5.38 g (33 mmol) | | |
| Carnitine salicylate | | | | 10 g (33 mmol) | |
| pH (NaOH) | qs pH 6 | qs pH 6 | qs pH 6 | qs pH 6 | qs pH 6 |
| Water | qs 100 g | qs 100 g | qs 100 g | qs 100 g | qs 100 g |

Procedure

Place five locks of damaged hair (2.7 g/25 cm; alkaline solubility of 60) on a hot plate kept at a temperature of 27° C. and covered with a food film. Apply 0.5 g of formula (formulae 7 to 11) to be tested/g of hair to five distinct locks. Spread the formula to be tested over the lock using a small brush. Leave to stand for 5 minutes. Dry under a hood (60° C., 10 min/g hair). Repeat the steps so as to have a total of 5 applications of the formula to be tested. Leave the locks suspended vertically for 24 h. Then comb the locks 30 times with a comb at a rate of 10 cm/s. Weigh the mass of hair lost during the combing.

Results

TABLE 6

| Formulae | Loss (g) |
| --- | --- |
| 7 (Comparative) | 0.3062 |
| 8 (Comparative) | 0.3461 |
| 9 (Comparative) | 0.3032 |
| 10 (Invention) | 0.1154 |
| 11 (Comparative) | 0.3724 |

The results show that there is less hair breakage when the locks are treated by means of a process according to the present invention.

Comparative Tests No. 4: Comparison of Various Carnitine Salicylate Derivatives—Study of the "Prevention of Breakage Due to Repeated Combing" Effect Formulae Tested:

The following formulae were prepared and then tested according to the procedure described below:

TABLE 7

| Ingredients | Formulae | | | |
| --- | --- | --- | --- | --- |
| | 12 (Invention) | 13 (Invention) | 14 (Invention) | 15 (Control) |
| Carnitine 3-methylsalicylate | 25 g | | | |
| Carnitine 2-hydroxy-3-methoxybenzoate | | 5 g | | |
| Carnitine 2-methoxybenzoate | | | 10 g | |
| $H_2O$/EtOH Mixture (Volume ratio 30/70) | qs 100 g | qs 100 g | qs 100 g | qs 100 g |

Procedure

Place four locks of damaged hair (2.7 g/25 cm; alkaline solubility of 60) on a hot plate kept at a temperature of 27° C. and covered with a food film. Apply 5 g of formula (formulae 12 to 15) to be tested/g of hair to four distinct locks. Spread the formula to be tested over the lock using a small brush. Leave to stand for 10 minutes. Dry under a hood (60° C., 10 min/g hair). Repeat the steps so as to have a total of 5 applications of the formula to be tested. Leave the locks suspended vertically for 24 h. Then comb the locks 30 times with a comb at a rate of 10 cm/s. Weigh the mass of hair lost during the combing.

Results

TABLE 8

| Formulae | Loss (g) |
| --- | --- |
| 12 (Invention) | 0.1795 |
| 13 (Invention) | 0.1686 |
| 14 (Invention) | 0.2090 |
| 15 (Control) | 0.3830 |

The results show that there is less hair breakage when the locks are treated by means of a process according to the present invention.

Comparative Tests No. 5: Evaluation of the Persistence with Respect to Shampoo Washes of the "Prevention of Breakage" Effect by Means of the Flexabrasion Test Formulae Tested:

The following formulae were prepared and then tested according to the procedure described below:

TABLE 9

| | Formulae | |
|---|---|---|
| Ingredients | 16 (Invention) | 17 (Placebo) |
| Carnitine salicylate | 18 g | — |
| H$_2$O/EtOH Mixture (Volume ratio 80/20) | qs 100 g | qs 100 g |
| pH | pH 6 | pH 6 (Addition HCl) |

Procedure

Place a lock of damaged hair (150 mg/27 cm; alkaline solubility (AS) of approximately 40) in a chute. The AS 40 locks are prepared by three successive bleachings starting from natural hair. Pour 0.5 g of formula (formula 16) to be tested/g of hair into the chute, massage the lock so as to thoroughly distribute the formula over the lock. Leave to stand for 5 minutes on a hot plate kept at a temperature of 27° C. Dry under a hood (60° C., 10 min/g hair). Repeat the steps so as to have a total of 5 applications of the formula to be tested. Then wash the lock according to the washing protocol described below.

Washing Protocol:

Wet the locks with tap water at 38° C. for 10 seconds, apply the DOP shampoo (0.4 g/g of hair), massage for 15 seconds and rinse carefully with water for 20 seconds. Repeat the preceding shampooing protocol three times. End with a fifth shampoo wash with Elsève Multi-vitamin 2-in-1 shampoo using the same protocol. Wring the lock dry. Comb. Dry under a hood (60° C., 10 min/g hair).

The placebo lock was prepared by following the same procedure as described above, using formula 17. Furthermore, a control (nontreated) lock was washed 4 times with the DOP shampoo and once with the Elsève Multi-vitamin 2-in-1 shampoo according to the washing protocol described above. The lock according to the invention, the placebo lock and the control lock were tested according to the Flexabrasion test described below.

Flexabrasion Test

The Flexabrasion technique is known to those skilled in the art for the breakage of keratin fibers (references: Flexabrasion: A Method for Evaluating Hair Strength, Cosmetics & Toiletries Journal, Jun. 26, 2009 and Hair Breakage in Normal and Weathered Hair: Focus on the Black Patient, Journal of Investigative Dermatology Symposium Proceedings, Volume 12, Issue 2, December 2007, Pages 6-9). The principle of the test is to measure the time taken for hair fibers subjected to a mechanical stress to break (flexure and abrasion). A Flexabrasion device (Fiberstress model from the company Textechno) is used. A strand of hair is attached to a 20 g weight at one end and the other end is attached to an immobile bar. The strand of hair moves back and forth on a 300 µm stainless steel wire. The movement has an amplitude of 10 mm and a frequency of 0.5 Hz. The breakage is detected by an optical sensor which measures the breakage time (in seconds). A series of measurements comprises 25 strands of hair.

Results

TABLE 10

| Formulae | Median drop time (s) |
|---|---|
| 16 (Invention) | 1286 |
| 17 (Placebo) | 656 |
| Control | 394 |

The results show that, even after 5 shampoo washes, there is still a better performance quality in terms of prevention of hair breakage compared with the placebo and control. Thus, the treatment process according to the invention is particularly resistant to shampoo washes.

Comparative Tests No. 6: Evaluation of the Persistence with Respect to Shampoo Washes of the "Prevention of Breakage" Effect by Means of the Cyclic Fatigue Test Formulae Tested:

The following formulae were prepared and then tested according to the procedure described below:

TABLE 11

| | Formulae | |
|---|---|---|
| Ingredients | 18 (Invention) | 19 (Placebo) |
| Carnitine salicylate | 10 g | — |
| H$_2$O/EtOH Mixture (Volume ratio 80/20) | qs 100 g | qs 100 g |
| pH | 6.0 | pH 6 (Addition HCl) |

Procedure

Place a lock of damaged hair (150 mg/27 cm; alkaline solubility (AS) of approximately 40) in a chute. The AS 40 locks were prepared by three successive bleachings starting from natural hair. Pour 0.4 g of formula (formula 18) to be tested/g of hair into the chute, massage the lock so as to thoroughly distribute the formula over the lock. Leave to stand for 5 minutes on a hot plate kept at a temperature of 27° C. Dry under a hood (60° C., 10 min/g hair).

Washing Protocol:

Wet the locks with tap water at 38° C. for 10 seconds, apply the DOP shampoo (0.4 g/g of hair), massage for 15 seconds and rinse carefully with water for 20 seconds. Repeat the preceding shampooing protocol three times. End with a fifth shampoo wash with Elsève Multi-vitamin 2-in-1 shampoo using the same protocol. Wring the lock dry. Comb. Dry under a hood (60° C., 10 min/g hair).

The placebo lock was prepared by following the same procedure as described above, using formula 19. The lock according to the invention and the placebo lock were tested according to the cyclic fatigue test described below.

Cyclic Fatigue Test:

The cyclic fatigue technique is known to those skilled in the art for the breakage of keratin fibers (reference: https://www.diastron.com/app/uploads/2017/06/Dia-Stron-CYC801-Brochure.pdf). The principle of the test is to measure the number of cycles of extension of a single fiber before breakage. Fibers 30 mm long are subjected to a constant stress (100 MPa) at a constant rate (40 mm/s). The studies are carried out at 25° C. and 45% relative humidity. A Diastron CYC801 device (from the company Diastron) is used. A series of measurements comprises 50 strands of hair.

17

Results

TABLE 12

| Formulae | Number of cycles before breakage (average) |
| --- | --- |
| 18 (Invention) | 29 520 |
| 19 (Placebo) | 6123 |

The results show that there is less hair breakage when the locks are treated by means of a process according to the present invention.

Additional Tests: Evaluation of the Persistence with Respect to Shampoo Washes of the "Prevention of Breakage" Effect of Carnitine Gallate by Means of the Flexabrasion Test Formula Tested:

The following formula was prepared and then tested according to the procedure described below:

TABLE 13

| Ingredients | Formula 20 (Invention) |
| --- | --- |
| Carnitine gallate | 5 g |
| H₂O/EtOH Mixture (Volume ratio 80/20) | qs 100 g |

Procedure

Place a lock of damaged hair (150 mg/27 cm; alkaline solubility (AS) of approximately 20) in a chute. Pour 0.4 g of formula (formula 20) to be tested/g of hair into the chute, massage the lock so as to thoroughly distribute the formula over the lock. Leave to stand for 5 minutes on a hot plate kept at a temperature of 27° C. Dry under a hood (60° C., 10 min/g hair). Repeat the steps so as to have a total of 5 applications of the formula to be tested. Then wash the lock according to the washing protocol described below.

Washing Protocol:

Wet the locks with tap water at 38° C. for 10 seconds, apply the DOP shampoo (0.4 g/g of hair), massage for 15 seconds and rinse carefully with water for 20 seconds. Repeat the preceding shampooing protocol three times. End with a fifth shampoo wash with Elsève Multi-vitamin 2-in-1 shampoo using the same protocol. Wring the lock dry. Comb. Dry under a hood (60° C., 10 min/g hair). The lock according to the invention was tested according to the Flexabrasion test described in comparative tests No. 5.

Results

TABLE 14

| Formula | Median drop time (s) |
| --- | --- |
| 20 (Invention) | 1234 |

The results show that, even after 5 shampoo washes, there is still a good performance quality in terms of prevention of hair breakage for formula 20. Thus, the treatment process according to the invention using a composition comprising carnitine gallate is particularly resistant to shampoo washes.

18

The invention claimed is:

1. A method for washing or conditioning hair with a composition (A), comprising a step of:
    (i) applying to the hair the composition (A) comprising at least one compound selected from formulae (Ia), (Ib), (Ic), (Id), (Ie), or mixtures thereof:

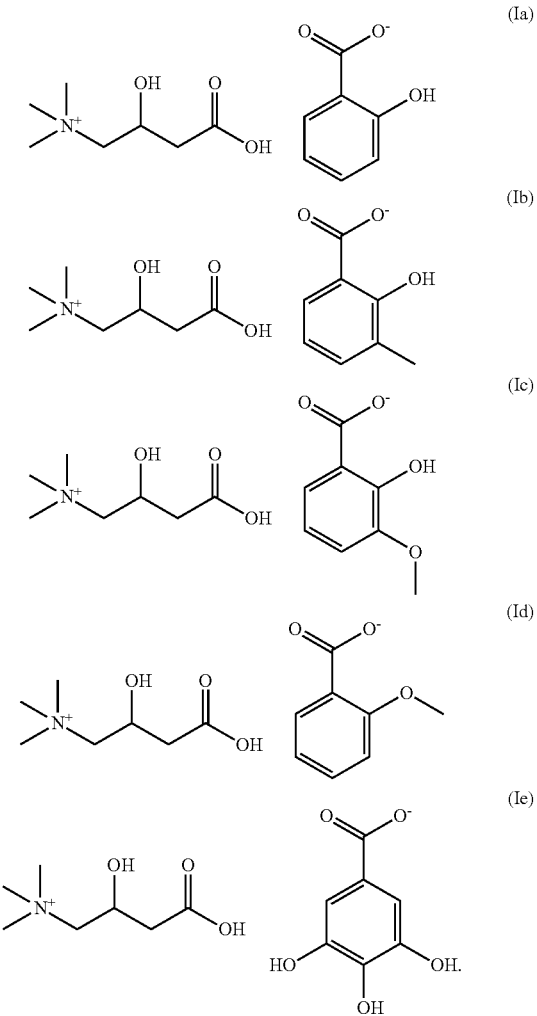

2. The method of claim 1, wherein the cationic portion of the at least one compound is in the form of an optical isomer of L or D configuration.

3. The method of claim 1, wherein the composition (A) comprises a total content of at least one compound of formula (I) ranging from 0.5% to 50%, by weight, relative to the total weight of composition (A).

4. The method of claim 1, wherein the composition (A) comprises a solvent selected from water, $C_2$-$C_4$ alcohols, polyols, polyol ethers, or mixtures thereof.

5. The method of claim 1, wherein the composition (A) comprises a solvent comprising water and ethanol, wherein the solvent comprises at least 10% ethanol by weight, relative to the total weight of the solvent.

6. The method of claim 1, wherein the composition (A) is applied to dry hair.

7. The method of claim 1, further comprising at least one of steps (ii), (iii), and/or (iv), after step (i), wherein if two or more steps (ii), (iii), and/or (iv) are performed, the two or more steps are performed in any order after step (i):

(ii) leaving the composition (A) on the hair for a period of at least 10 seconds;
(iii) rinsing and/or washing the hair; or
(iv) drying the hair.

* * * * *